(12) United States Patent
Nagel et al.

(10) Patent No.: US 8,051,697 B2
(45) Date of Patent: Nov. 8, 2011

(54) SELF CALIBRATION DEVICES FOR CHEMICAL AND BIO ANALYTICAL TRACE DETECTION SYSTEMS

(75) Inventors: David J. Nagel, Falls Church, VA (US); R. Andrew McGill, Lorton, VA (US); Patrick M. Mills, Arlington, VA (US); Rekha Pai, Alexandria, VA (US)

(73) Assignees: The George Washington University, Washington, DC (US); The United States of America as represented by the Secretary of the Navy, Washington, DC (US)

( * ) Notice: Subject to any disclaimer, the term of this patent is extended or adjusted under 35 U.S.C. 154(b) by 429 days.

(21) Appl. No.: 12/252,537

(22) Filed: Oct. 16, 2008

(65) Prior Publication Data

US 2009/0205398 A1    Aug. 20, 2009

Related U.S. Application Data

(60) Provisional application No. 60/980,447, filed on Oct. 17, 2007.

(51) Int. Cl.
*G01N 37/00* (2006.01)
(52) U.S. Cl. ............................. 73/1.03; 73/1.02; 73/1.07
(58) Field of Classification Search .......... 73/1.02–1.03, 73/1.06–1.07
See application file for complete search history.

(56) References Cited

U.S. PATENT DOCUMENTS

| | | |
|---|---|---|
| 2002/0123048 A1 | 9/2002 | Gau |
| 2003/0004403 A1 | 1/2003 | Drinan |
| 2005/0130292 A1 | 6/2005 | Ahn et al. |
| 2008/0049551 A1* | 2/2008 | Muyzert et al. ................. 367/24 |

* cited by examiner

*Primary Examiner* — Thomas P Noland
(74) *Attorney, Agent, or Firm* — Blank Rome LLP

(57) ABSTRACT

The present invention relates to chemical and bioanalytical sensors and sensor systems, particularly to systems incorporating a calibration device for sensors where the calibration device is comprised of an array of micromachined MEMS structures and materials for trapping and retaining calibrant or interferant materials until they are needed and released quantitatively using structure operatively associated with the array.

12 Claims, 2 Drawing Sheets

E = C(CF_3)_2OH

SELF CALIBRATION DEVICES FOR CHEMICAL AND BIO ANALYTICAL TRACE DETECTION SYSTEMS

CROSS REFERENCE TO RELATED APPLICATIONS

This application claims the benefit of the filing date and right of priority under 35 USC 119(e) of U.S. Provisional 60/980,447, filed 17 Oct. 2007, the contents of which is incorporated herein its entirety.

STATEMENT REGARDING FEDERALLY SPONSORED RESEARCH OR DEVELOPMENT

The granting agency and grant number for the federal government funds used in researching or developing this invention is/are:
Names Of Parties to A Joint Research Agreement
The George Washington University
The Naval Research Laboratory

REFERENCE TO A SEQUENCE LISTING

A table or a computer list appendix on a compact disc
[ ] is
[X] is not
included herein and the material on the disc, if any, is incorporated-by-reference herein.

FIELD OF THE INVENTION

The present invention relates to sensors and sensor systems and, particularly to systems incorporating a calibration device for sensors, where the calibration device is composed of materials and/or structures for trapping and retaining calibrant and/or interferent materials until they are needed.

BACKGROUND OF THE INVENTION

Sensors and systems incorporating them generally put out voltages, frequency shifts or some other signals, rather than the amount of the physical, chemical or biological entity that is of interest to users. In order to recover the quantitative values of interest, for example, the concentration of a poisonous gas, it is necessary to employ a sensor calibration curve, which relates the signals that are not of direct utility to the amount (with proper units) of the entity being measured (the measurand). The measurement of a calibration curve requires producing and independently measuring the amount of the measurand, exposing the sensor or sensor system to that amount and reading the signal produced by the sensor or system. This is usually done at several values of the measurand in order to fit a mathematical curve to the data to produce the calibration curve.

For a variety of reasons, the performance of a sensor system can deviate from the calibration curve with age and the amount of use. It is necessary to be able to verify the performance of the sensor or system against the original calibration curve at various times during the lifetime of the sensor or system. This is especially true for instruments used by first responders, which may not be turned on for long intervals. However, it also applies to devices for screening of air passengers, which are used daily, and for process control, which requires continuous use for long periods. In all events, returning sensor systems to a laboratory for calibration checks is unacceptable because of cost reasons. It is highly desirable to be able to do performance or recalibrations in the field or factory.

In typical calibration, the first question is whether the instrument is working at all. This can be answered by turning on the device, and then seeing if the output has the correct value. The next question is whether or not the instrument responds reasonably to the chemical of interest. This can be answered by producing a vapor or mist of that chemical at the intake to the instrument to see if the output rises and falls with the appropriate time scale. The remaining question is whether or not the instrument is correct quantitatively. To answer this question, it is necessary to do a recalibration at a minimum of one point. As with any calibration, two numbers are needed, namely the value of the measurand and the amount of signal elicited by that amount. One way to obtain the amount of the measurand quantitatively is to produce and measure it independently, as noted above for obtaining the original calibration curve. This almost always requires returning the instrument to a calibration laboratory.

SUMMARY

In one preferred embodiment is provided a microelectromechanical device for calibration of a sensor, comprising: (i) an array of micromachined MEMS structures; and (ii) a calibrant releasing or interferent releasing structure operatively associated with the array.

In another preferred embodiment is provided a calibrant film (or interferent film) for calibration of a sensor, comprising: a polymeric film containing a calibrant wherein the film is fixed on a microelectrical-mechanical system (MEMS) array, and wherein the array comprises a heating element adjacent said film, and wherein heating of said film releases said calibrant.

In another preferred embodiment, the invention provides a composite film of at least two or more thicknesses wherein calibration using at least two or more films provides a sensitive calibration profile.

In another preferred embodiment is provided a calibrant reservoir (or interferent reservoir) for calibration of a sensor, comprising: (i) a canal or well (reservoir) within a MEMS array; (ii) a membrane covering said canal or well; and (iii) a rupture mechanism operatively associated with the membrane, wherein the membrane is capable of trapping a calibrant within the canal or well, and wherein upon rupture of the membrane the calibrant is released.

Another preferred embodiment provides wherein the rupture mechanism is an electronically actuated rupture device.

Another preferred embodiment provides wherein the rupture mechanism is an optically actuated rupture device.

Another preferred embodiment provides wherein the calibrant reservoir further comprises a heater device for heating the calibrant.

Another preferred embodiment provides wherein the reservoir well or canal comprises wells of at least two different sizes wherein calibration using the least different wells provides a sensitive concentration-to-volume calibration profile.

In another preferred embodiment, a retrofit unit is provided for calibration of existing sensors or sensor systems. Such a unit is provided for hand-held sensors, desktop sensors, and built-in sensors.

In another preferred embodiment, a slide-in replacement unit is provided for existing sensors as an improvement for

DETAILED DESCRIPTION OF THE INVENTION

Figure 1:
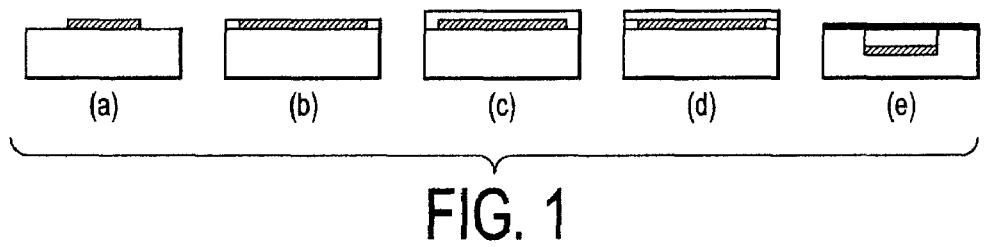
FIG. 1 is cross sectional diagram of five alternative geometries for storing calibrant molecules on or in substrates.
Figure 2:
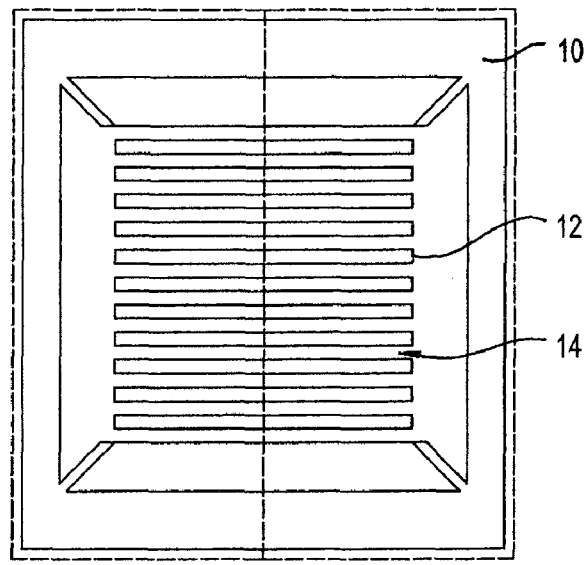
FIG. 2 is diagram of an example of a device of the present invention.
Figure 3:
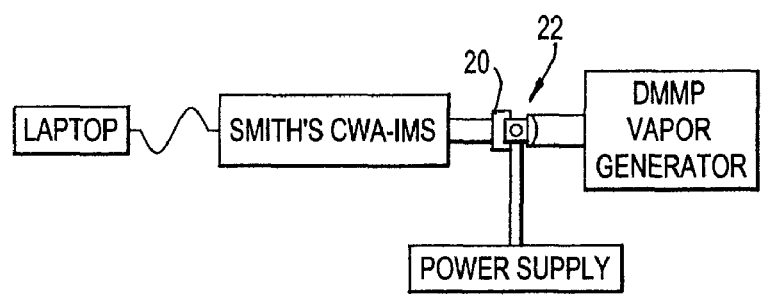
FIG. 3 is a diagram illustrates a testing of an example device of the present invention as described in FIG. 2.
Figure 4:
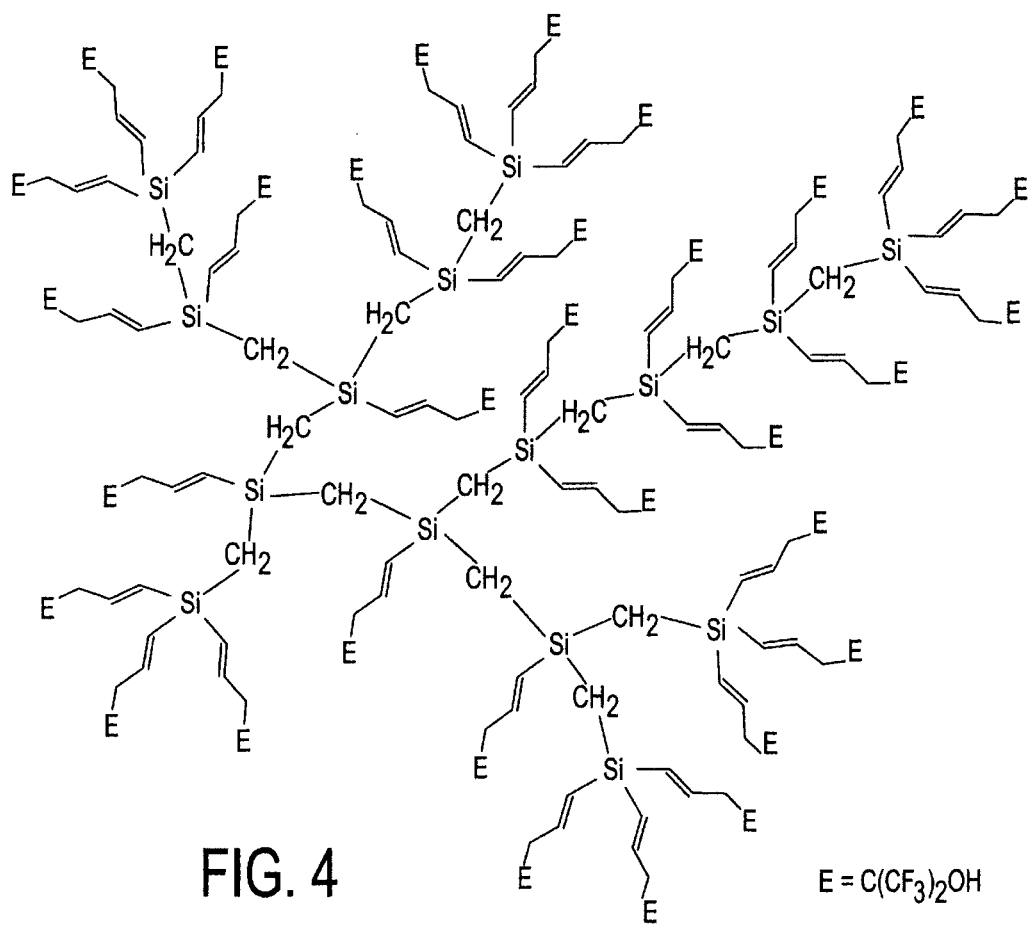
FIG. 4 is a graphic display of a polymer used in the example of FIG. 2.
Figure 5:
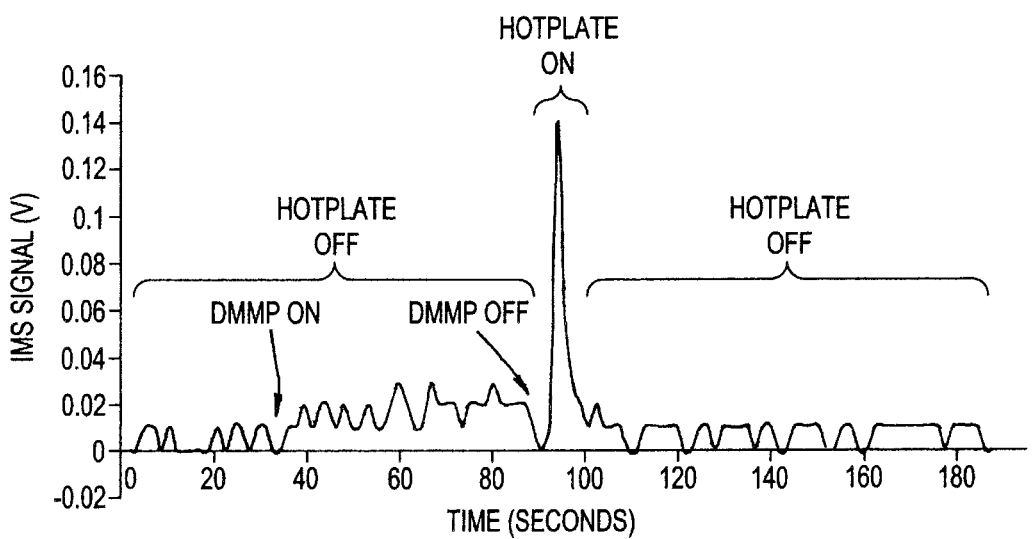
FIG. 5 is a diagram illustrating the results of the test performed as described in FIG. 3.

The present invention is directed to a device which includes a way to obtain the amount of measurand quantitatively in the field of use by producing a known value of the measurand by an alternative means without having to measure it. In the case of sensor instruments for simple organic and bio-chemicals and explosives, which operate by detecting and quantifying the concentration of the molecules of interest in a pneumatic fluid flowing in the system, it is necessary to be able to introduce a known number of molecules into a known amount of pneumatic fluid. Although air is used as the pneumatic fluid in the examples and description herein, the pneumatic fluid may be any liquid or gas. The purpose of this invention is to describe various means of doing so. Thus, one advantage of the present invention is in situ qualitative and quantitative calibration of chemical, explosive and biochemical trace detectors.

The amounts of materials of interest that are needed for an operational response test or for at least a one-point recalibration in the field are very small. The materials of interest, or simulant materials that mock their response, can be stored within many small regions inside of a detection instrument. Using micro-machining and related technologies, it is possible to make enough individual storage locations within a detection instrument that it would never need to be returned to a laboratory for recalibration. This might involve hundreds of material storage locations, for example, a square array of such locations with 20×20, or 400, storage locations. If each of the locations is smaller than 1 millimeter, for example, the total array would be about one inch square or less. Such a component then may be integrated or disposed within hand held or other portable instruments. The device that stores the material of interest (or its simulant) may be incorporated or disposed, for example, on the walls of the conduit through which the air to be measured moves to the sensor. The ability to produce a known concentration (for examples, molecules per volume of air) would depend on knowing how many molecules are released and the rate of airflow for the stream into which they are introduced. Both of these quantities can be measured independently in tests of the components that are described in this invention.

Three elements in the current invention include (a) storage structure to store known amounts of specific chemicals or biochemicals for long times, (b) release structure to release them quantitatively at desired times and (c) volume measuring structure to determine the volume of air into which the known number of molecules is released. The structure for releasing the chemicals, whatever their method of storage, can be accelerated, for example, by the deposition of thermal energy from either electrical or optical sources. The amount of air into which the calibrant molecules are released depends on the aperture (diameter, for example) of the conduit, the airflow rate and the rate of mixing of the calibrant molecules into the air stream. Each of these will be discussed in further detail below.

DEFINITIONS

The term "array" refers to microelectrical-mechanical system (MEMS) structures on a silicon or other substrate, made by micromachining. Multiple micro-units can constitute an array. For example, on a 6 mm×6 mm array, there would be multiple, i.e. over 40, 0.8 mm units.

The term "calibrant" refers to chemical and biochemical calibration materials, particularly those germane to national defense, homeland security, and industrial chemicals. Non-limiting examples include chemicals to be monitored in industrial processes such as CN, CH4, CO, chlorine, fluorine, SO2, HS, HCl, and others, therapeutics, pharmaceuticals, narcotics, restricted precursor chemicals, weapon agents such as sarin, VX, mustard gas, arsine, phosgene, tear and pepper gases, explosives like TNT and other nitrogen-based explosives, and incapacitating agents such as B2. Bioanalytes includes nucleic acids, amino acids, proteins, peptides, biopolymers, biowarfare agents, and biomaterials.

The term "interferent" refers to a substance that may erroneously affect analytical measurements. An interferent (often as a source of a determinant error), causes all of the readings to either be elevated or depressed. An example of an interferent might be, for example, ascorbic acid (vitamin C) if present within a blood sample when analysed for glucose content using an electrochemical glucose oxidase based biosensor. Ascorbic acid if present within the blood may cause all of the blood glucose measurements to be elevated. Yet another interferent can be acetaminophen when conducting blood glucose testing, or other blood analytes that affect measurements. Another example of an interferent might be volatile hydrocarbons, alone or in combination, such that they intefere with the detection of a hydrocarbon of interest, i.e ethanol breathalyzer testing affected by methanol or acetone. Alternatively, interferents such as latex paint fumes, ammonia, ammonia cleaning agents, airfresheners, engine exhaust and DEAE, might all affect measurements in chemical weapons detectors. Another example might be phosphorous compounds interfering with the detection of organophosphates in chemical weapons. As used herein, wherever calibrant is used, the term interferent can be added to or substituted therewith.

The term "film" or "tape" refers to polymers that can trap and release calibrants as described herein as would be known to persons of ordinary skill in this art. Non-limiting examples include polyimides, polyethylene glycols (PEG), monomethylether polyethylene glycols (MPEG), polypropylene glycols (PPG), polytetramethylene glycols (PTMEG), polymethylmethacrylates (PMMA), polystryenes (PS), MatrixDHB (dihydroxybenzoic acids), and MatrixCHCA (cyanohydroxycinnamic acids). The films or tapes may be transparent, naturallly opaque or rendered opaque.

The term "thickness" of the film refers to films ranging in thickness from about 1 micron to about 2 mm, and also from less than about 1 micron to about 1 mm, and also from about 1 to about 50 micrometers. Two or more thicknesses in a unit refers to films which release an amount corresponding to two or more data points along a calibration graph line for more accurate calibration of the sensor over a wider range.

Calibrant Storage Geometries and Materials

The substrates on which one or more calibrant materials may be stored individually or as mixtures and at one or more concentration levels, can be fixed within the instrument or can be movable. The quantitative loading of substrates maybe achieved by various means including, but not limited to, inkjetting, spin coating, or aerosol coating of quantitative prepared solutions of calibrant or calibrant and encapsulant material. Direct write techniques such as ink jetting are preferred as they can be more easily controlled to deposit known quantities of materials in specific locations with high precision to within a few microns of the target destination. From a knowledge of the solution concentration of calibrant and the number of drops of known size deposited in one location, the amount of calibrant deposited in one area can be computed. In an arrayed type calibrant system, one of many calibrant doses may be sacrificed in the laboratory setting to validate the performance of the calibrant system and effectively calibrate the calibration system.

We will first discuss fixed embodiments and then describe devices in which the substrate can be moved to bring fresh calibrant into contact with the airflow.

In a fixed environment, the materials for recalibration can be put on surfaces, within layers that may or may not have a covering layer or in small wells or canals inside of a substrate that may or may not be covered by a membrane that can be ruptured to release the chemicals at will. The membrane may also serve the purpose to provide a controlled diffusion release of calibrant analyte. The actuation of an appropriate valve could seal the calibrant source until required.

For example, FIG. 1 is cross sectional sketches of five non-limiting examples of alternative possible geometries for storing calibrant molecules (shown as hatched) on or in substrates (shown as the large open boxes at the bottom of each figure). From left to right: (a) the calibrant is on the surface of the substrate and uncovered, (b) the calibrant is dissolved into a thin film on the substrate, (c) the film containing the calibrant has a cover layer of the same material, (d) the film containing the calibrant has a cover layer of a different material and (e) the calibrant resides within compartments (wells or canals) in the surface of the substrate and is covered with a membrane that will be ruptured for release of the calibrant. The compartments can be partially filled (as sketched) or entirely filled with the calibrant.

Geometry (a) is well suited for materials with very low vapor pressures. Otherwise, the calibrant molecules may leak off the surface, which may introduce background noise in any measurement made with the instrument and also may vitiate the ability to introduce a known number of molecules into the airflow at a desired time.

Geometry (b) includes the use of a film into which the calibrant molecules either is dissolved or, in the case of a porous film, is wicked into interstities. Polymer films that absorb molecules of interest are known for many analytes. However, again there is the possibility of loosing molecules out of the film by slow diffusion over long times. Hence, a cap on the part of the thin solvent film may be provided to slow leakage due to diffusion to a negligible rate. That cap can be the same materials as the solvent film, as shown in geometry (c), or a different material, as shown in geometry (d). A capping film of a different film may be preferred as it allows very little diffusion.

Like geometries (b), (c) and (d), geometry (e) is preferred for materials of widely diverse vapor pressures. Here, like the fourth geometry, the membrane over the wells containing the calibrant can be made of a very impermeable material. If the vapor pressure is high and the number of calibrant and gaseous molecules in the appropriate ratios, the calibrant will be released when the restraining membrane is ruptured. If the vapor pressure is low or the calibrant cannot be entirely vaporized within the well, then it will be necessary to use two steps to release it, membrane rupture and heating, either sequentially or simultaneously.

Non-limiting examples of sorbent materials for trapping analytes using geometries (b), (c) or (d), for example, are described in an article by McGill et al. in Chemtech, Vol. 24, No. 9, 27-37 (1994). These materials and other materials, such as related polymers, can be used as relatively thick coatings (for example, 1 micron to 2 mm thick) to effectively trap an analyte indefinitely until substantially heated to release the trapped analyte. The sealant membrane that may be ruptured on demand can be formed from a barrier material such as a metal or polymer that on heating to a certain temperature melts and flows to form an open hole over which it previously sealed the exit of a calibrant.

For geometry (e), the membrane covering the well containing the calibrant molecules may be one layer of a single material or multiple materials. The material(s) can be of any type, including but not limited to, polymers, glasses or metallic materials. The membrane material(s) are preferably such that the diffusion of calibrant molecules through the membrane will cause the loss of less than about 1% of the trapped molecules over the desired shelf and use life of the recalibration method. The thickness may be on the order of one to fifty micrometers, although other thicknesses are part of this invention. The cross section of the membrane need not be uniform. Any tension parallel to the surface of the membrane is suitable, although high tensions are preferred to insure fast rupture of the membrane when a release is desired.

For movable substrates on which the calibrant materials are stored, all the same configurations represented in FIG. 1 are again possible. The main difference being that the movable substrate is physically realigned with a localized heating source to limit heating to a specific small zone of the movable substrate that contains a specific quantity of the calibrant analyte to be released into the pneumatic delivery system of the detector being tested. Various movable substrates are possible including, but not limited to, tape and disc mechanisms.

In a tape delivery technique the calibrant analyte can be preloaded into or onto the tape using, for example, any of the various geometries described in FIG. 1. If calibrant is preloaded into the tape then this may be accomplished by using a thermoplastic tape that is heated under analyte loading and cooled to ambient temperature to fix the analyte in the tape. The tape under ambient conditions is of a plastic nature and offers very low analyte diffusion, and under relatively high temperatures becomes porous, or rubbery and porous, and allows rapid release of analyte. An example of a tape mechanism may include a simple heating source that contacts the tape on demand and elevates the tape temperature to the required temperature to rapidly release the stored analyte. The tape technique offers an approach that could provide many calibrant analyses depending on the length of the tape. Different analyte types may be preloaded into the tape at different positions or as mixtures at one location. For tapes that act as a support for the calibrant and other possible related materials, metallic or plastic tapes may be utilized, for example.

In a disc delivery technique the calibrant analyte can be preloaded into or onto the disc using, for example, any of the various geometries described in FIG. 1. The substrate may consist of a variety of materials. One example, a silicon wafer, may be fabricated with a variety of microfabrication techniques to contain multiple wells at known locations which are locally addressable. These wells may be sealed with materials discussed earlier and analyte released by thermally heating the sealing layer to eliminate the seal or to accelerate diffusion through the sealant or membrane. The localized heating may be simply achieved with a laser of a suitable wavelength to heat or melt the calibrant, membrane, or encapsulant.

Calibrant Release Techniques.

The calibrant chemical molecules stored in a detection instrument in any of the manners described above must be released on demand. This can be accomplished by heating the regions in which the molecules are stored by electrical or optical means and/or by rupturing the cover membrane. The rupture can be achieved without a significant increase of the pressure within the well, by directing energy onto the membrane, or by causing a rapid pressure increase within the sealed well, leading to the mechanical failure of the membrane and release of its calibrant molecules. Localized heating may release the calibrant molecules by their thermal agitation through melting and vaporizing, or by removing the encapsulant or covering membrane.

Several electrical configurations are possible. For example, wires may be microfabricated into the substrates that hold the calibrant molecules or else are present on a nearby substrate which, when heated, will radiatively, convectively or conductively heat the region containing the calibrant molecules and release them. Microfabricated or other wires on or below a restraining membrane, or on the walls or bottom of a well, are possible embodiments. For an array of calibrant molecules, a multiplexed set of highly conductive wires leading to local heating elements made out of less conductive materials may be provided, for example, in an address structure.

Several optical configurations for heating the desired region are also possible. One example includes laser sources of any kind, light emitting diodes and other solid-state optical emission sources, and any type or size of light bulb. Any of these sources can be used by itself or with lenses to focus the light onto the desired region containing the calibrant molecules. The optical sources and calibrant patches may be fixed or movable relative to each other. The optical heater and the calibrant patch may have any relative geometry. The number of optical sources may range from one to as many as there are calibrant storage elements. The calibrant molecules can be stored on the surface of any of the optical sources. For example, a dense array of solid-state lasers would permit placing the calibrant molecules directly on the output surfaces of the lasers by ink jetting or other means described above.

This invention embraces the use of electrical or optical heating pulses of any duration. The time duration of the electrical or optical heating pulses must be precisely controlled in order to produce a release in a short time, usually less than one second, without damage to the calibrant material(s).

In alternative embodiments, the temperature of the device may be controlled by incorporation of a heater, for example a serpentine platinum heater trace fabricated on, or into, the substrate or elsewhere within the geometry of the device.

When a calibrant is release instantaneously, such as by rupturing a cover membrane, precise diffusion and other mixing of the material into the air stream may not always be possible even in a turbulent air flow regime. Thus, in one embodiment controlled delivery of the calibrant into the air stream may be preferred. For example, a permeable or semipermeable membrane may be provide through which the calibrant can be release, such as by the application of heat to the membrane, in a controlled manner providing a determinable and known flux of calibrant through the membrane and into the air stream. Thus, calibrant concentration measurements taken over time can be analyzed, rather than merely assessing the concentration of the calibrant by virtue of a spike in concentration due to an instantaneous release of calibrant material into the air stream.

For example, calibrant analyte can be released directly into an air stream of the detector by permeation through the cover layer or membrane. Provided the temperature of the calibrant analyte and membrane are kept constant, then the flux of the calibrant analyte through the membrane, i.e., concentration of calibrant released through the membrane overtime, will remain constant. The flux of calibrant is controlled by the temperature of the calibrant source and membrane and the surface area of the membrane. A slow release of calibrant analyte over time provides sufficient source calibrant remaining in the device. In this mode of operation, a single calibrant source may provide enough calibrant for the calibration feature of the detector to have an operation life comparable with the detector. The flux of the calibrant under various temperatures may be verified and calibrated under laboratory conditions such that the in situ release of calibrant over time at various temperatures may be known in advance.

Multiple calibrant sources, perhaps on multiple devices, may be loaded with a variety of calibrant analytes and be independently controlled by independent heating of each source or each device. To provide suitable temperature control of a microfabricated device, heating with power consumption constraints is preferred. Heating control can be achieved, for example, using pulsed width modulation feedback control, when the resistance of the heating element is used to determine the temperature of the device. The thermal heat consumption of the device may be optimized by providing a thermal insulator for the structure, for example, by suspending the substrate from a silicon frame or other frame to thermally isolate the structure.

Given that the calibrant device can generate a constant flux of analyte into the air stream of the detector, the air flow rate is constant, and either turbulent flow exists or diffusion time are adequate for thorough mixing, then a constant calibrant flux into the air flow stream can be actuated by thermal control of the calibrant device. If calibrant bleed, or leaking, is a problem prior to intended actuation, a valve may be added to isolate the calibrant device.

Control of Air Volume

Sensors to be calibrated are sensitive to the concentration of the molecules of interest, here the calibrant molecules. Concentration is the ratio of the number of molecules to the volume of the air containing them. The means of storing and releasing a known number of molecules were already described.

The volume of air to which the released calibrant molecules have access is determined by the airflow rate over the surface from which the molecules emerge upon release. Diffusion of molecules within the air is generally small for normal flow rates, but can be a definite for mixing within small or constricted channels. Convective mixing can be important in determining the volume of air containing the released molecules.

The volume of air that passes over the surface from which the calibrant molecules are emitted for some period of time depends on the cross sectional area of the conduit and the velocity of air flow through the conduit during that time. The air flow channels for calibration may be different than the air sample channel(s) employed during normal operation of the analyteical instrument containing the detector to be calibrated. If so, the instrument may have pneumatic switches that redirect the air flow when a recalibration event is triggered. While the conduit's geometry is usually fixed, the flow rate can be controlled, for example, by varying the speed of the fan that induces the air motion.

The cross sectional geometry of the air conduit over the release surface can have any shape. However, it is preferable to have a rectangular or nearly rectangular geometry with the dimension perpendicular to the airflow direction and parallel to the release surface longer than the dimension in the directional normal to the release surface. In this case, the broad release area favors more rapid introduction of large numbers of calibrant molecules. In case a small dimension perpendicular to both the air flow and the release surface is preferred, the distance normal to the release surface into which the calibrant molecules have to mix is minimized, which promotes achievement of the desired uniform distribution of those molecules. The air conduit may have alternative geometries, such as serpentine paths. Also, blades or meshes or other structures or geometries may be provided within the airflow to promote mixing or restrict flow.

The air flow rate traveling past the calibrant device may be alternatively determined by an additional sensor. An example of a flow sensor could be a hot wire anemometer or thermal conductivity sensor. This sensor may be integrated into the same substrate containing the calibrant analyte.

It is possible to calculate the volume of air into which the calibrant molecules are released. However, the air volume accessible to the calibrant molecules may also be determined by laboratory calibration using a fast sensor of known response to validate the performance of the calibrant system and effectively calibrate the calibration system. This is the preferred approach. It has the additional virtue of directly determining the calibrant concentration from only the measurement of the molecules release based on a fixed air flow rate, rather than independent measurement of both the number of molecules released and the air volume into which they are released during calibration.

EXAMPLES

A microfabricated hotplate device coated with a NRL HCSA2 Polymer (illustrated in FIG. 4) was used to trap a quantity of dimethylmethylphosphonate (DMMP) vapor analyte calibrant. A diagram of the device is illustrated in FIG. 2. After collection, the hotplate was heated by passing electrical current through the device to release all the DMMP into an adjacent lightweight chemical detector (LCD) ion mobility spectrometer (IMS), as illustrated in the diagram of FIG. 3.

The LCD produced a signal response to allow verification or non-verification of the characteristic response to DMMP. For the IMS, the characteristic drift time for DMMP was confirmed so no recalibration of the instrument was required. The results are displayed in FIG. 5.

As illustrated in FIG. 2, the device tested was composed of sorbent coated dual serpentine platinum heaters supported by a 6 μm thick layer of polyimide suspended over a silicon frame. More particulary, the device includes a frame 10, Cr (200Å)/Pt (1650Å) 35 Micron width Electrodes 13 and and approximately 5.6 μm Thick Polyimide Diaphragm 14 Coated with a 2 micron thick layer of NRL HCAS2 Loaded with DMMP calibrant. The calibrant device was designed to allow analyte flow normal to the surface and through a 10×23 array of 375 μm×125 μm perforations in the polyimide heater support. This facilitates relatively large airflow through the device with a low pressure drop. In preliminary experiments, the device was demonstrated by interfacing to the front end of a commercial IMS, as illustrated in FIG. 3. Initial experiments focused on use of Smith's LCD-IMS, Testing was done with dimethylmethylphosphate (DMMP), and the Plastic chuck 20 was machined to house CASPAR. It should be noted that the present inventive subject is similarly applicable to devices having a preconcentrator in front of the sensor/detector.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

The invention claimed is:

1. A microelectromechanical device for calibration of a sensor, comprising: (i) an array of micromachined MEMS structures for storage of calibrant molecules; and (ii) a calibrant releasing or interferent releasing structure operatively associated with the array.

2. The device of claim 1, further comprising wherein the calibrant releasing or interferent releasing structure is a film that comprises a polymeric film containing a calibrant or interferent wherein the film is fixed on a microelectrical-mechanical system (MEMS) array, and wherein the array comprises a heating element adjacent to said film, and wherein heating of said film releases said calibrant or interferent, and wherein the film comprises at least two or more films of differing thicknesses wherein calibration using the at least two or more films provides a sensitive calibration profile.

3. The device of claim 1, wherein the calibrant releasing or interferent releasing structure is a reservoir that comprises (i) a canal or well within a MEMS array; (ii) a membrane covering said canal or well; and (iii) a rupture mechanism operatively associated with the membrane, wherein the membrane is capable of trapping a calibrant or interferent within the canal or well, and wherein upon rupture of the membrane the calibrant or interferent is released, and wherein the reservoir well or canal comprises wells of at least two different sizes wherein calibration using the at least two different wells provides a sensitive concentration-to-volume calibration profile.

4. A film for calibration of a sensor, comprising: a polymeric film containing a composition selected from a calibrant or an interferent wherein the film is fixed on a microelectrical-mechanical system (MEMS) array, and wherein the array comprises a heating element adjacent said film, and wherein heating of said film releases said calibrant or interferent composition.

5. A calibrant or interferent reservoir for calibration of a sensor, comprising: (i) a canal or well within a MEMS array; (ii) a membrane covering said canal or well; and (iii) a rupture mechanism operatively associated with the membrane, wherein the membrane is capable of trapping a calibrant or interferent within the canal or well, and wherein upon rupture of the membrane the calibrant or interferent is released.

6. The calibrant reservoir of claim 5, wherein rupture mechanism is an electronically actuated rupture device.

7. The calibrant reservoir of claim 5, wherein rupture mechanism is an optically actuated rupture device.

8. The calibrant reservoir of claim 5, further comprising a heater device for heating the calibrant.

9. A retrofit unit for a sensor, comprising: a) housing suitable for operational integration with an existing sensor; and b) a microelectromechanical device for calibration of a sensor, comprising: an array of micromachined MEMS structures; and a calibrant releasing or interferent releasing structure operatively associated with the array.

10. The retrofit unit of claim 9, wherein the existing sensor is selected from the group consisting of hand-held sensors, desktop sensors, and built-in sensors.

11. A slide-in replacement for a sensor, comprising: a) housing suitable for operational replaceable integration with an existing sensor; and b) a microelectromechanical device for calibration of a sensor, comprising: an array of micromachined MEMS structures; and a calibrant releasing or interferent releasing structure operatively associated with the array.

12. The slide-in replacement unit of claim 11, wherein the existing sensor is selected from the group consisting of handheld sensors, desktop sensors, and built-in sensors.

* * * * *